United States Patent
Lai et al.

(10) Patent No.: US 6,739,870 B2
(45) Date of Patent: May 25, 2004

(54) USE OF FINITE ELEMENT ANALYSIS FOR ORTHODONTIC MECHANICS AND APPLIANCE SELECTION

(75) Inventors: Ming-Lai Lai, Arcadia, CA (US); Andrew W. Chen, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 159 days.

(21) Appl. No.: 09/965,707

(22) Filed: Sep. 26, 2001

(65) Prior Publication Data

US 2003/0059736 A1 Mar. 27, 2003

(51) Int. Cl.[7] .................................................. A61C 3/00
(52) U.S. Cl. ........................................................ 433/24
(58) Field of Search .................................. 433/24, 213

(56) References Cited

U.S. PATENT DOCUMENTS 5,454,717 A * 10/1995 Andreiko et al. ............. 433/24
5,616,866 A * 4/1997 Murakami .................... 73/804
5,975,893 A * 11/1999 Chishti et al. ................. 433/6
6,471,511 B1 * 10/2002 Chishti et al. ................ 433/24
2001/0002310 A1 5/2001 Chishti et al. ................ 433/24

FOREIGN PATENT DOCUMENTS

WO  WO 00/19931  4/2000

* cited by examiner

Primary Examiner—John J. Wilson
(74) Attorney, Agent, or Firm—James D. Christoff

(57) ABSTRACT

An effective orthodontic treatment is determined by storing an original position model of a patient's teeth. The patient's teeth are then displayed according to the original position model, and appliances are selected according to a proposed orthodontic treatment. A final position model of the patient's teeth is also stored, and the selected appliances are displayed based upon the final position model. A finite element analysis is performed based on the proposed orthodontic treatment and on a movement of the patient's teeth from the final position to the original position in order to determine stresses, strains, forces, and/or moments on the appliances and on the patient's teeth and bone. If the stresses, strains, forces, and/or moments are not optimized, a new orthodontic treatment is proposed and the process is repeated.

15 Claims, 4 Drawing Sheets

USE OF FINITE ELEMENT ANALYSIS FOR ORTHODONTIC MECHANICS AND APPLIANCE SELECTION

TECHNICAL FIELD OF THE INVENTION

The present invention relates to the use of a finite element analysis in order to design and/or select orthodontic appliances.

BACKGROUND OF THE INVENTION

Orthodontics is a branch of dentistry that involves the movement of malpositioned teeth to orthodontically correct positions. Before prescribing an orthodontic treatment, X-rays and photographs of the patient's teeth and jaw structure are usually taken. Also, a mold of the patient's teeth is typically made. This mold along with the X-rays and photographs provide a model of the positions of the patient's teeth and dental arches prior to treatment.

The orthodontist also relies on a post treatment model of the desired positions of the patient's teeth and dental arches. This post-treatment model has typically been a mental model formulated in the mind of the orthodontist based on the orthodontist's experience and skill. However, computer programs are also known to assist the orthodontist in the development of a computerized post-treatment model. The orthodontist then devises an initial treatment strategy to move the patient's teeth and/or dental arches from their positions as represented by the pre-treatment model to the desired positions as represented by the post-treatment model.

In order to implement the initial treatment strategy, the orthodontist applies various orthodontic appliances to the patient's teeth. In a typical treatment, brackets are attached to anterior, cuspid, bicuspid, and molar teeth. An archwire is then be held to the brackets by ligatures so that the archwire forms a track to guide movement of the brackets and the associated teeth to desired positions for correct occlusion. The brackets, archwires, ligatures, and other ancillary devices used in correctly positioning teeth are commonly referred to as "braces".

The orthodontist's treatment strategy frequently requires correction of the relative alignment between the upper and lower dental arches. For example, certain patients have a condition referred to as a Class II malocclusion in which the lower dental arch is located an excessive distance in a rearward direction relative to the location of the upper dental arch when the jaws are closed. Other patients may have an opposite condition referred to as a Class III malocclusion in which the lower dental arch is located in a forward direction of its desired location relative to the position of the upper dental arch when the jaws are closed.

Orthodontic treatment of Class II and Class III malocclusions are commonly corrected by movement of the upper and lower dental arches as units relative to one another. To this end, forces are often applied to each dental arch as a unit by applying a force to the brackets, the archwires, and/or ancillary devices applied to the dental arch. In this manner, a Class II or Class III malocclusion can be corrected at the same time that the archwires and the brackets are used to move individual teeth to desired positions relative to each other.

Corrections of Class II and Class III malocclusions are sometimes carried out by use of other devices such as headgear that include strapping which extends around the rear of the patient's head. The strapping is often coupled by tension springs to the brackets, archwires, and/or ancillary devices. For correction of Class III malocclusions, the strapping can be connected by tension springs to a chin cup that externally engages the patient's chin. In either instance, the strapping and springs serve to apply a rearwardly directed force to the associated jaw.

Instead of using headgear which is often considered unsatisfactory because it is visibly apparent, many practitioners and patients favor the use of intra-oral devices for correcting Class II and Class III malocclusions. Such devices are often located near the cuspid, bicuspid, and molar teeth and away from the patient's anterior teeth. As a result, intra-oral devices for correcting Class II and Class III malocclusions are hidden in substantial part once installed.

Orthodontic force modules made of an elastomeric material have also been used to treat Class II and Class III malocclusions. Pairs of such force modules are coupled between the dental arches on opposite sides of the oral cavity. Elastomeric force modules may be used in tension to pull the jaws together in a direction along reference lines that extend between the points of attachment of each force module. Such force modules may be O-rings or chain-type modules each made of a number of integrally connected O-rings. These modules are typically removable by the patient for replacement when necessary, since the module may break or the elastomeric material may degrade during use to such an extent that the amount of tension exerted is not sufficient. Non-removable intra-oral devices are also known which rely on flexible members that are connected to upper and lower dental arches of a patient. Moreover, telescoping tube assemblies that may be used to urge the dental arches toward positions of improved alignment are known.

As can be seen, there are a wide variety of orthodontic appliances that are available to an orthodontist in the implementation of a treatment strategy. However, few, if any, tools exist to assist the orthodontist in the accurate selection of appliances that are likely to effectively implement the orthodontist's initial treatment strategy. Moreover, few, if any, tools exist to allow the orthodontist to accurately predict the effectiveness of the initial treatment strategy. Therefore, the treatment strategy is frequently modified over time as the orthodontist observes the actual movement of the teeth and dental arches in response to the orthodontist's treatment strategy.

The use of a finite element analysis has been known in the area of orthodontics. For example, U.S. Pat. No. 5,131,844 discloses that a finite element structural model of an individual tooth or a set of teeth may be developed to determine stress distributions under various loading conditions. This patent suggests that such a model may then lead to new approaches to the testing of dental materials, the studying of the effects of bite dislocations, and the determination of proper restorative conditions. This patent further suggests that the model can be used for the design of prosthodontics. U.S. Pat. No. 4,975,052 discloses that a finite element model has been used to determine the optimum angles for a retractor assembly. It is also known to use a finite element analysis to determine how loads applied to brackets generate tensile stresses in the material of the brackets.

However, a finite element analysis has not been used to study the interaction between orthodontic appliances and teeth in order to develop an effective orthodontic treatment strategy.

SUMMARY OF THE INVENTION

In accordance with one aspect of the present invention, a method of analyzing an orthodontic treatment comprises the following: modeling first positions of a patient's teeth; modeling desired second positions of the patient's teeth; and, performing a finite element analysis based on the orthodontic treatment and a movement of the patient's teeth between the first and second positions.

In accordance with another aspect of the present invention, a method of determining an effective orthodontic treatment comprises the following: a) creating a first model based upon first positions of a patient's teeth; b) creating a second model based upon second positions of the patient's teeth, wherein the second positions represent desired positions of the patient's teeth; c) selecting a proposed set of orthodontic appliances according to a proposed orthodontic treatment; d) performing a finite element analysis based on the proposed orthodontic treatment and a movement of the patient's teeth between the first and second positions; e) selecting a new set of orthodontic appliances if the finite element analysis indicates that the proposed orthodontic treatment produces undesired effects; and, f) repeating d) and e) as necessary until the effective orthodontic treatment is achieved.

In accordance with yet another aspect of the present invention, a computer readable storage medium has program code stored thereon which, when executed by a computer, performs the following tasks: a) storing a first position model of a patient's teeth; b) storing a second position model of the patient's teeth, wherein the second position model represents desired positions of the patient's teeth; c) storing a set of orthodontic appliances; d) applying the set of orthodontic appliances to the patient's teeth according to one of the first and second position models; and, e) performing a finite element analysis based on the first position model, the second position model, and the applied set of orthodontic appliances.

In accordance with still another aspect of the present invention, a method, implemented with the assistance of a computer, of determining an effective orthodontic treatment comprises the following: a) storing first positions of a patient's teeth; b) displaying the patient's teeth according to the first positions; c) selecting orthodontic appliances according to a proposed orthodontic treatment of the patient's teeth; d) storing second positions of the patient's teeth, wherein the second positions are desired positions; e) installing the selected orthodontic appliances on the patient's teeth in the second positions; and, f) performing a finite element analysis to assess effects on the orthodontic appliances and on the patient's teeth based on the first and second positions and on the proposed orthodontic treatment.

BRIEF DESCRIPTION OF THE DRAWING

These and other features and advantages will become more apparent from a detailed consideration of the invention when taken in conjunction with the drawings in which.

DETAILED DESCRIPTION

Figure 1:
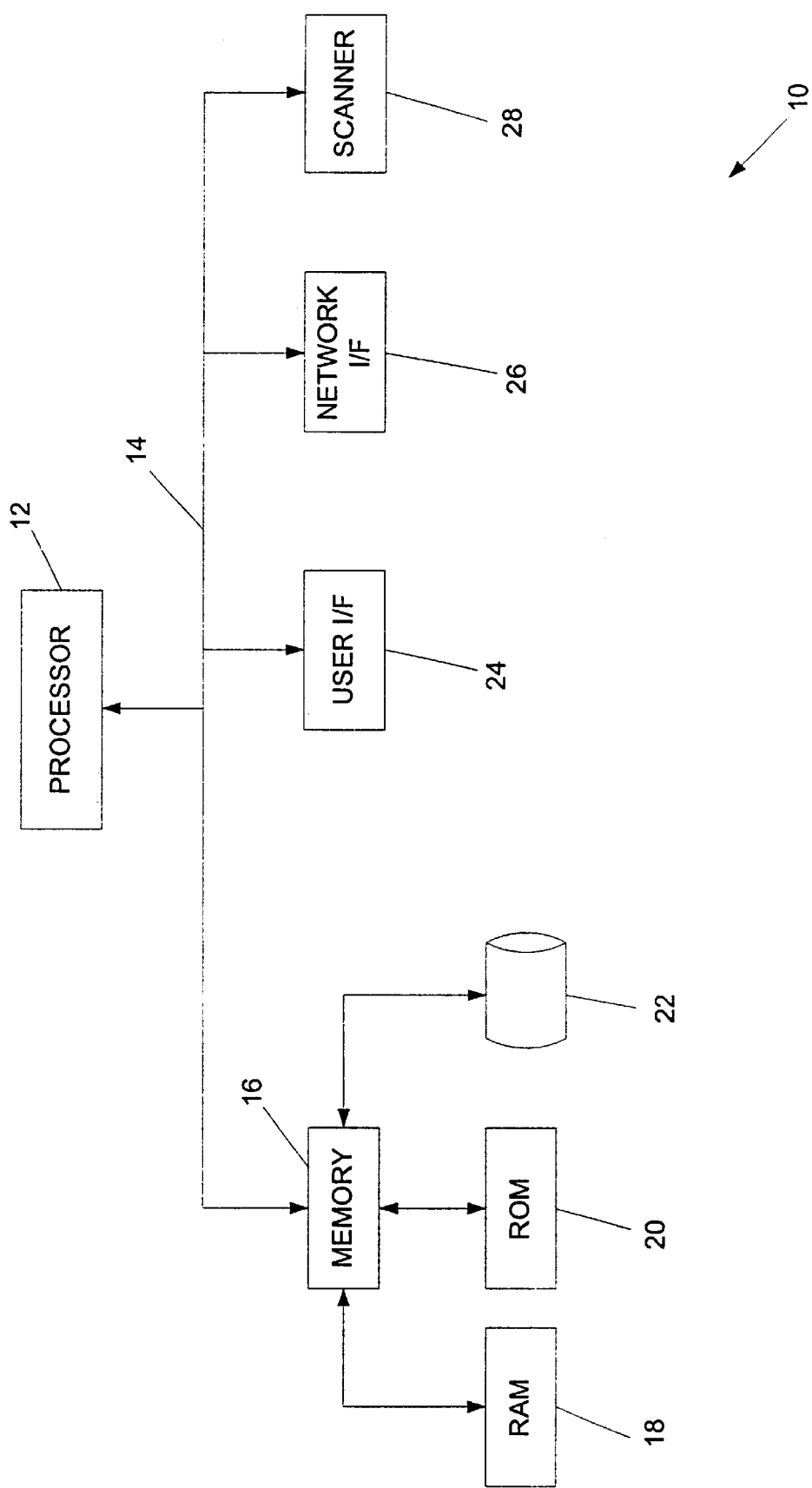
FIG. 1 is a block diagram of a computer system useful in implementing the present invention; and, FIGS. 2A, 2B, and 2C are a flow chart representing a program that may be executed by the computer system of FIG. 1 in order to implement the present invention.

FIG. 1 shows a simplified block diagram of a data processing system 10 that may be used to implement an orthodontic treatment development program in accordance with the present invention. The data processing system 10 typically includes at least one processor 12 which communicates with a number of peripheral devices by way of a bus system 14. The bus system 14 can include a local bus and one or more expansion buses (e.g., ADB, SCSI, ISA, EISA, MCA, NuBus, or PCI), as well as serial and parallel ports. However, any suitable bus configuration may be used for the bus system 14.

The peripheral devices typically include a memory system 16 having a RAM storage 18, a ROM storage 20, and a file storage 22. The peripheral devices typically also include a user interface 24 and a network interface 26. The user interface 24 includes connections to such user interface devices as a keyboard, a mouse, a printer, a video monitor, speakers, etc. The network interface 26 includes modems for connections to external machines such as network servers, web sites, other users, etc. The data processing system 10 can be implemented as personal computer, a workstation, a mainframe, etc.

The RAM storage 18 may be used to store instructions and data during program execution, and the ROM 20 may be used to store fixed instructions such as the operating system of the data processing system 10. The file storage 22 provides non-volatile storage for programs and data files, and typically includes one or more hard disk drives, one or more floppy disk drives, one or more CD drives, one or more removable media cartridge drives, and/or the like.

A scanner 28 may be used for scanning the patient's teeth or casts of the patient's teeth. The scans may be provided as a data set to the data processing system 10 for further processing in accordance with a program 100 shown in FIGS. 2A, 2B, and 2C. The scanner 28 may be coupled to a port of the data processing system 10 so that it can communicate the scanned data set directly to the processor 12 through the bus system 14. Alternatively, the scanner 28 may be located at a remote location and may communicate the scanned data set to the data processing system 10 by way of the network interface 26.

Figure 2A:
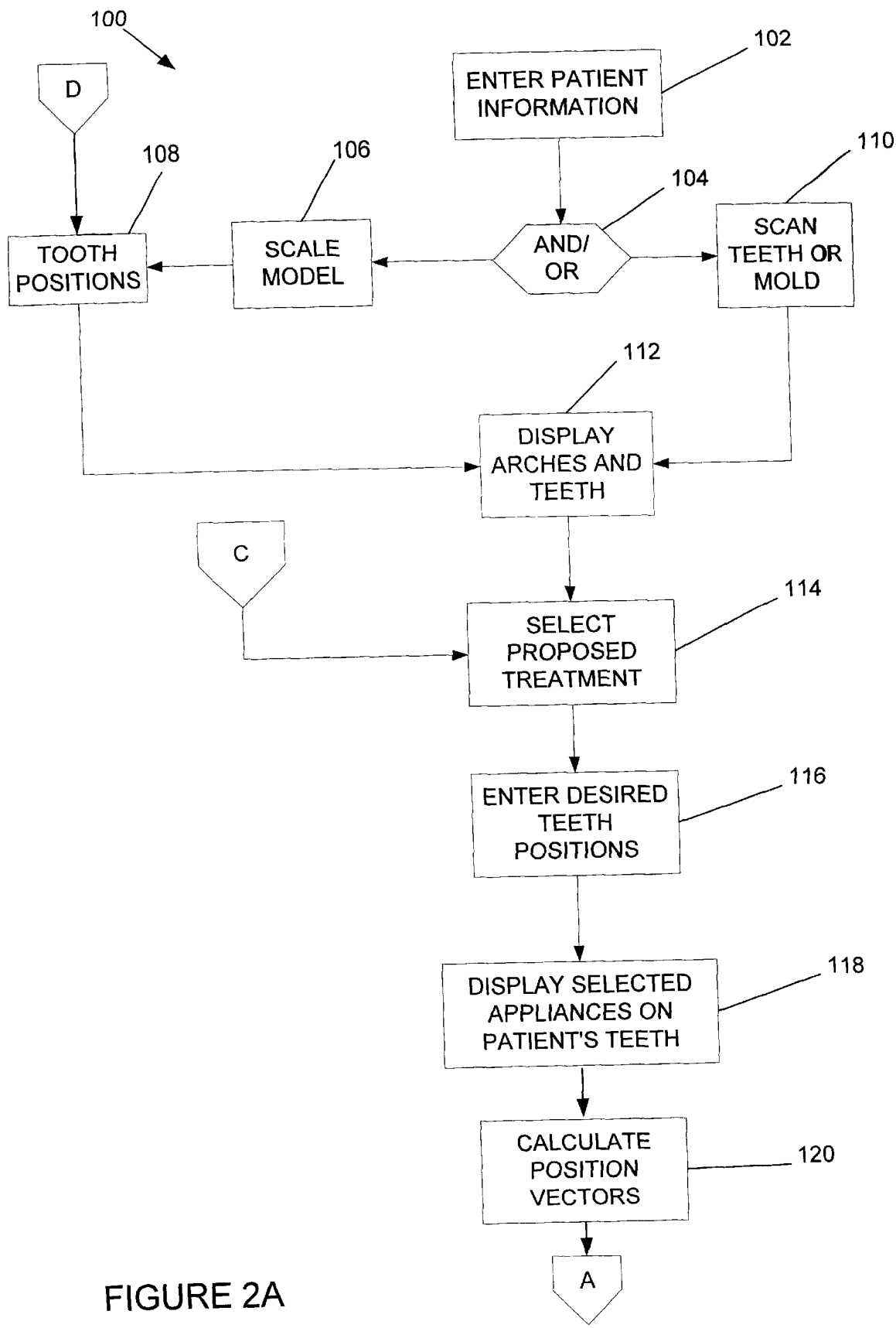
Figure 2B:
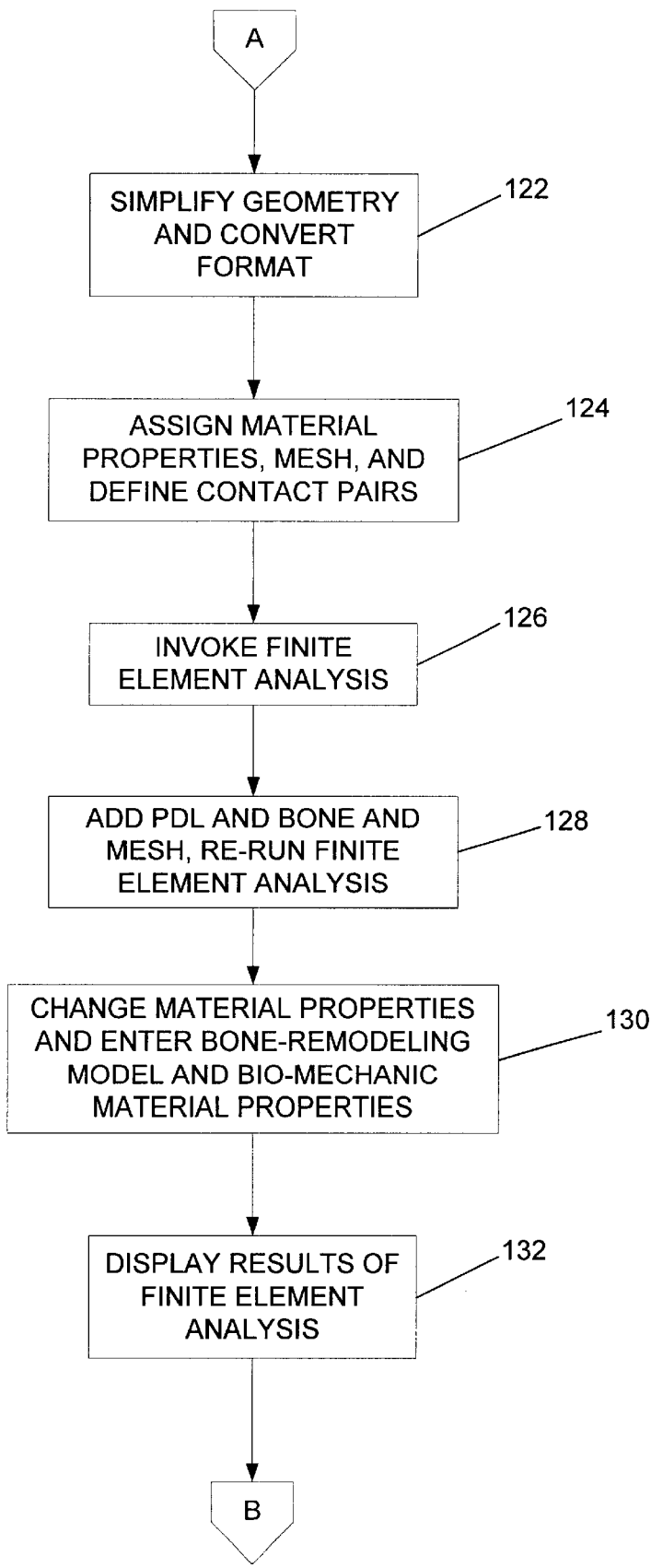
Figure 2C:
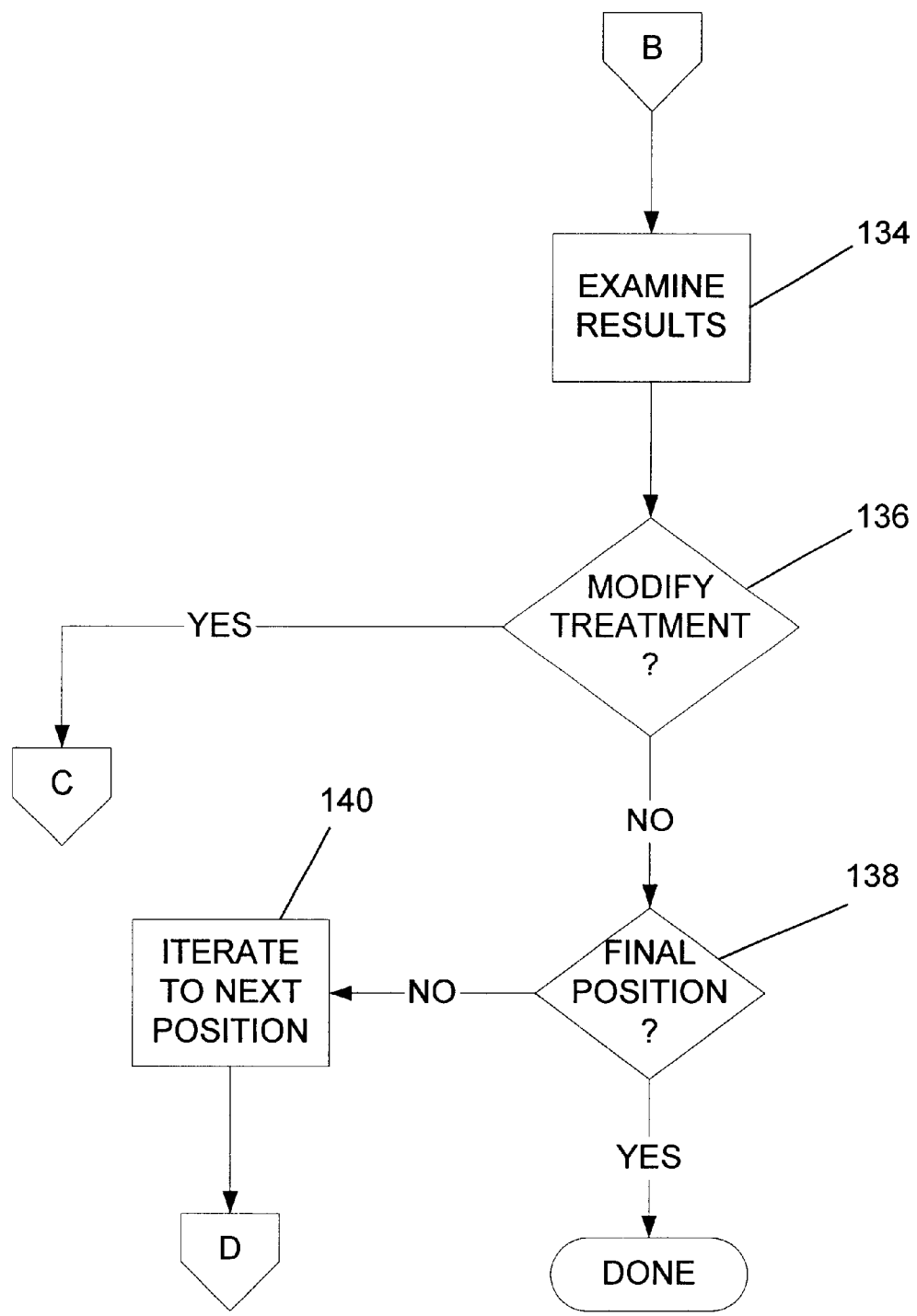

The data processing system 10 executes the program 100 shown in FIGS. 2A, 2B, and 2C. The user of the program 100 may be the orthodontist who is developing an orthodontic treatment for a patient. However, other users can include clinicians, assistants of the treating orthodontist, orthodontic product developers, etc.

At a block 102 of the program 100, the appropriate patient information is entered and stored for later use. Such information can include tooth size, upper and lower dental arch sizes, malocclusion type, age, gender, and/or any patient information that is desired or relevant. Next, a pre-treatment model of the patient's teeth and/or dental arches is entered. At a block 104, the program 100 may be arranged to offer a choice between methodologies for entry of this model. For example, a scale model of the teeth may be generated automatically or manually and may be entered at a block 106 and stored in the memory system 16, and the positions of the patient's teeth may be entered or calculated and stored in the memory system 16 at a block 108. Additionally or alternatively, the patient's teeth or a mold of the patient's teeth may be scanned through use of the scanner 28 and the resulting scanned data set, which may include tooth size, tooth position, and/or shapes of the dental arches, may be stored in the memory system 16 at a block 110.

Following processing of the blocks 106, 108, and/or 110, the upper and lower dental arches, their relative positions, and the positions of the patient's teeth are displayed at a block 112. This display may be used to facilitate the initial selection of a prescription, brackets, archwires, ligatures, and/or other orthodontic appliances by the orthodontist in accordance with the orthodontist's proposed orthodontic treatment to achieve the desired results. These initial selections are entered and stored in the memory system 16 at a block 114. The orthodontist's proposed orthodontic treatment strategy will typically be based on the orthodontist's experience.

However, the program 100 at the block 114 may instead be arranged to make the initial prescription and appliance selections automatically by comparing the pretreatment model entered at the blocks 106, 108, and/or 110 to treatment data stored in the memory system 16. This treatment data, for example, may be in the form of a look up table or other data structure containing past pre-treatment models and the corresponding orthodontic treatment strategies which were used to successfully treat the patients from whom the past pre-treatment models were derived. Thus, the current patient's pre-treatment model may be used as an address into the memory system 16 in order to read out the treatment strategy corresponding to this address. Extrapolation can be used in the case where a patient's pre-treatment model is not an exact match with the stored pre-treatment models.

At a block 116, the desired final positions of the patient's teeth, based on the prescription, the patient's arch shapes, archwire shapes, tooth size, etc., are entered and stored in the memory system 16. The desired final positions of the patient's teeth may be referred to herein as the post-treatment model.

Intermediate positions of the patient's teeth may also be entered and stored at the block 116. One or more such intermediate positions of the patient's teeth are optionally employed where the orthodontist's proposed treatment strategy includes the re-positioning of the patient's teeth in stages, where each stage may involve the replacement or modification of selected appliances such as force modules and/or archwires, where each stage involves the employment of different force levels, where the orthodontist intends to use appliances whose geometries or properties change over time and may need to be replaced during treatment, and/or the like. As an example, nitinol archwires have memory which must be taken into account when moving the patient's teeth from their final positions to their original positions during execution of the program 100. Therefore, if nitinol archwires are used, the material properties of the archwires must be changed according to un-loading stress-strain curves during movement of the teeth to the intermediate positions.

At a block 118, the program 100 applies the initially selected appliances to the patient's teeth when the teeth are at their desired final positions for full expression of the teeth. The program 100 at the block 118 then displays the initially selected appliances applied to the patient's teeth when the teeth are at their desired final positions.

Accordingly, the program 100 has stored both the pre-treatment model and the post-treatment model for the patient. At this point, the program 100 at a block 120 calculates and stores position vectors for each of the patient's teeth. Each position vector points from the original position in the pre-treatment model to the final position in the post-treatment model for the corresponding tooth.

The program 100 at a block 122 simplifies the tooth and appliance geometry and converts the format of the resulting data file for use by a finite element analysis. The simplification processing of the block 122 is executed in order to compress the data so as to reduce the amount of computing power required for downstream processing. This simplification, for example, may involve simplifying the tooth geometry by flattening of the occlusal surfaces of the teeth and by simplifying the geometry of the brackets. Alternatively, other data compression techniques may instead be used. In any event, given sufficient computing power, the simplification processing may be omitted so that the block 122 simply converts the data file format to one used by the finite element analysis which is executed downstream, as discussed below.

A finite element analysis such as Abaqus or Ansys may be used by the program 100. These finite element analysis programs are general purpose finite element analysis programs that can be used by the program 100 to determine the stresses, strains, forces, friction, and moments on the selected orthodontic appliances and on the patient's teeth, PDL (periodontic ligament structure), and bone. Finite element analysis programs specifically written for orthodontic applications can also be employed.

At a block 124 of the program 100, material properties are assigned for the appliances selected at the block 114. The appliance material properties may be stored in a data base of the memory system 16 and may be automatically accessed from the data base based upon the appliances selected at the block 114. Alternatively, the material properties for the appliances selected at the block 114 may be manually entered at the block 124. The material properties for appliances may require entry each time that the treating orthodontist changes appliances during treatment. For examples, archwires of different thicknesses and/or metals may be changed one or more times during treatment. Also, the archwires may be bent into different geometries one or more times during treatment. Each such change may require entry of new appliance material properties.

Also, at the block 124, material properties are assigned for the patient's teeth. The material properties of the patient's teeth may be stored in a data base of the memory system 16 and may be automatically accessed from the data base based on tooth type entered at the block 114. Alternatively, the material properties for the patient's teeth may be manually entered at the block 124.

Also, the program 100 at the block 124 meshes all components (teeth and appliances) except for the target surfaces of the contact pairs if the contact surfaces are assumed to be rigid. Non-rigid contact pairs can be meshed. Meshing is typically done by finite element analysis programs prior to the launching of the analysis itself. The block 124 may use a typical mesh, or the block 124 may implement one of the automatic mesh generators known in the art.

Moreover, contact pairs are defined at the block 124. A contact pair includes the surfaces of two appliances that contact each other. For example, the archwire and each bracket form corresponding contact pairs, the archwire and each of the ligatures that holds the archwire to a corresponding bracket form other corresponding contact pairs, and the brackets and ligatures form still other corresponding contact pairs. By convention, one of the appliances of a contact pair forms a contact surface and the other of the appliances of the contact pair forms a target surface. For self-ligating brackets, the archwire and the caps or clips form yet other corresponding contact pairs. All such contact pairs are defined at the block 124 by identifying and quantifying the areas of the contact surfaces of the contact pairs. Finally, if non-self-ligating brackets are proposed for use on the patient, an artificial cap for each bracket is attached at the block 124 to the top of the bracket archwire slot in order to prevent the archwire from coming out of the archwire slot during movement of the teeth.

The finite element analysis is then launched at a block 126 by moving the teeth, as represented by the data stored in the memory system 16, along the position vectors from their desired final positions in the post-treatment model to their original positions in the pre-treatment model. This run of the finite element analysis determines how the archwires will deform as the teeth move along the position vectors.

Then, at a block 128, data related to the patient's PDL and bone are added to the data relating to the patient's teeth. Also, PDL and bone material properties are entered at the block 128 and are meshed. These properties may be based on published PDL and bone material properties. (See, for example, C. Bouravel, et al., "Simulation of Orthodontic Tooth Movements," Journal of Orofacial Orthopedics, 1999.) The finite element analysis is re-run at this point in order to determine the stresses, strains, forces, friction, and moments that will be exerted on the appliances, teeth, the PDL for each tooth, and the bone by the deforming of the archwires as determined during execution of the block 126. Prior to re-running the finite element analysis at the block 128, however, the caps which were added at the block 124, if any, should be removed, and any elastomeric ligatures to be used in the proposed orthodontic treatment should be meshed to any non-self-ligating brackets.

If intermediate positions are included in the proposed orthodontic treatment, it may be necessary at the block 128 to finish execution of the finite element analysis at each intermediate position between the final and original positions for processing by a block 130. The block 130 is used in the case where the orthodontist uses intermediate positions during treatment as discussed above. For example, the material or geometric properties of relevant appliances (such as nitinol archwires) must be changed when the appliances are changed. Also, a bone-remodeling model and biomechanic material properties for PDL and bone (which are available from numerous publications such as J. Middleton, et al., "The Role of the Periodontal Ligament in Bone Modeling: The Initial Development of a Time-Dependent Finite Element Model," Amer. Jour. of Orthod. Dentof. Orthop., February 1996, pp. 155–162) are entered at the block 130 in order to take into account changes in PDL and bone during treatment. For example, as a tooth moves, bone in front of the moving tooth may dissolve and bone behind the moving tooth may grow. These changing bone properties and the resulting changing bone geometry are modeled at the block 130 to predict tooth movement versus time. However, as indicated above, the processing of the block 130 may be omitted if desired.

At a block 132, the teeth and appliances are displayed along with the stresses, strains, forces, friction, and moments determined by the finite element analysis. This display is examined at a block 134. If, as indicated by a block 136, the treatment strategy requires modification because the stresses, strains, forces, friction, and/or moments displayed at the block 132 are excessive or are outside desired ranges or because the force levels become ineffective, the treatment strategy is changed and the processing of the blocks 114–136 is repeated using the modified treatment strategy. The treatment strategy may require modification, for example, in the case where the stress on an appliance or tooth or bone is excessive or insufficient or in the case where the strain on a ligament is excessive or insufficient.

At this point, if only two positions (original and final) are required for a successful treatment, processing may be terminated. Accordingly, a block 138 determines if there are other positions in the treatment strategy that have not yet been processed. If so, a block 140 initiates another iteration of the program 100 in order to move the teeth to the next position and flow proceeds to the block 108 to implement the next iteration of the program 100. However, if the block 138 determines that there are no other positions to be processed, processing is terminated.

Certain modifications of the present invention have been discussed above. Other modifications will occur to those practicing in the art of the present invention. For example, the blocks 134 and 136 may be executed manually or they may be executed automatically by comparing the calculated stresses, strains, forces, friction, and/or moments to acceptable or desired ranges and by selecting appliances targeted to bring any errant stresses, strains, forces, friction, and/or moments within the desired and/or acceptable ranges.

Moreover, the present invention has been described above in relation to certain orthodontic appliances. However, it should be noted that the present invention may be used in connection with other orthodontic appliances such as retainers, closing loops, Class II correctors, chains and/or other elastomeric products, headgear, facebows, springs, and/or positioners such as those described in U.S. Pat. Nos. 5,975,893 and 6,227,851.

Furthermore, the terms "first positions" and "second positions" have been used herein in relation to positions of a patient's teeth with respect to an orthodontic treatment. It should be understood, however, that either of these first or second positions may be the original positions of a patient's teeth, the final positions of a patient's teeth, or any intermediate positions of a patient's teeth.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

We claim:

1. A computer implemented method of analyzing an orthodontic treatment comprising:

storing first positions of a patient's teeth in memory;

storing second positions of the patient's teeth in the memory, wherein the second positions comprise desired positions relative to the first positions; and, performing a finite element analysis based on the orthodontic treatment and a movement of the patient's teeth from the second positions to the first positions so as to produce information relative to the effectiveness of the orthodontic treatment.

2. The computer implemented method of claim 1 further comprising displaying the information.

3. The computer implemented method of claim 1 wherein the orthodontic treatment is based upon a set of orthodontic appliances to be applied to the patient's teeth, and wherein the performing of the finite element analysis comprises performing the finite element analysis based upon the set of orthodontic appliances and the movement of the patient's teeth from the second positions to the first positions.

4. The computer implemented method of claim 1 wherein the performing of the finite element analysis comprises:

determining position vectors for each of the patient's teeth between the first and second positions; and, performing the finite element analysis based on the orthodontic treatment and a movement of the patient's teeth along the position vectors.

5. The computer implemented method of claim 4 wherein the orthodontic treatment is based upon a set of orthodontic appliances to be applied to the patient's teeth, and wherein the performing of the finite element analysis comprises performing the finite element analysis based upon the set of orthodontic appliances and the movement of the patient's teeth from the second positions to the first positions.

6. The computer implemented method of claim 1 wherein the first positions of the patient's teeth are original positions, and wherein the second positions of the patient's teeth are final positions.

7. The computer implemented method of claim 1 wherein the first positions of the patient's teeth are intermediate positions, and wherein the second positions of the patient's teeth are final positions.

8. The computer implemented method of claim 1 wherein the performing of the finite element analysis comprises:
   storing material properties of the patient's teeth, PDL, and bone, and of the proposed orthodontic treatment in the memory; and,
   performing the finite element analysis based on the orthodontic treatment, the stored material properties, and a movement of the patient's teeth between the first and second positions.

9. A computer implemented method of analyzing an orthodontic treatment comprising:
   storing first positions of a patient's teeth in a computer readable memory;
   storing second positions of the patient's teeth in the memory, wherein the second positions comprise positions of the patient's teeth that are more desired than the first positions;
   storing material properties of the patient's PDL and bone in the memory;
   performing a first finite element analysis based on the orthodontic treatment and a movement of the patient's teeth from the second position to the first position;
   performing a second finite element analysis based on the assigned material properties and a movement of the patient's teeth to a third position between the first and second positions; and,
   displaying information relating to results of at least one of the first and second finite element analyses.

10. The computer implemented method of claim 9 wherein the performing of a second finite element analysis comprises performing the second finite element analysis based on the assigned material properties, properties of appliances used during the orthodontic treatment, and a movement of the patient's teeth to a third position between the first and second positions.

11. The computer implemented method of claim 9 wherein the orthodontic treatment is adjusted based on mechanics at the third position as indicated by results from the second finite element analysis.

12. The computer implemented method of claim 11 wherein the mechanics comprise force on the patient's teeth.

13. The computer implemented method of claim 11 wherein the mechanics comprise force on the patient's bone.

14. The computer implemented method of claim 11 wherein the mechanics comprise stress/strain on the patient's teeth.

15. The computer implemented method of claim 11 wherein the mechanics comprise stress/strain on the patient's PDL and bone.

* * * * *